United States Patent
Anderson et al.

(10) Patent No.: US 7,295,131 B2
(45) Date of Patent: Nov. 13, 2007

(54) DIAGNOSTIC SYSTEM FOR DETECTING RUPTURE OR THINNING OF DIAPHRAGMS

(75) Inventors: William Thomas Anderson, Chanhassen, MN (US); Christopher Ashley Wells, Eden Prairie, MN (US)

(73) Assignee: Rosemount Inc., Eden Prairie, MN (US)

( * ) Notice: Subject to any disclaimer, the term of this patent is extended or adjusted under 35 U.S.C. 154(b) by 275 days.

(21) Appl. No.: 11/031,953

(22) Filed: Jan. 7, 2005

(65) Prior Publication Data

US 2006/0152380 A1  Jul. 13, 2006

(51) Int. Cl.
*G08B 21/00* (2006.01)

(52) U.S. Cl. .................. 340/679; 340/657; 73/715

(58) Field of Classification Search ............. 340/679, 340/539.1, 544, 545.4, 562, 657; 73/715, 73/718; 92/49, 89, 96
See application file for complete search history.

(56) References Cited

U.S. PATENT DOCUMENTS

| | | | |
|---|---|---|---|
| 3,353,025 A | 11/1967 | Sturm | 250/215 |
| 3,946,726 A | 3/1976 | Pikul | 128/2.08 |
| 3,968,693 A | 7/1976 | Kazahaya | 73/398 |
| 4,206,761 A | 6/1980 | Cosman | 128/660 |
| 4,281,666 A | 8/1981 | Cosman | 128/748 |
| 4,571,537 A | 2/1986 | Taylor | 323/326 |
| 4,653,508 A | 3/1987 | Cosman | 128/748 |
| 4,660,568 A | 4/1987 | Cosman | 128/748 |
| 4,777,826 A | 10/1988 | Rud, Jr. et al. | 73/708 |
| 4,934,902 A * | 6/1990 | Mantell | 417/63 |
| 4,971,523 A | 11/1990 | Wacker et al. | 417/63 |
| 5,097,712 A | 3/1992 | Gerst et al. | 73/708 |
| 5,524,492 A | 6/1996 | Frick et al. | 73/706 |
| 5,760,310 A | 6/1998 | Rud, Jr. et al. | 73/706 |
| 6,003,380 A * | 12/1999 | Sasaki et al. | 73/720 |
| 6,029,525 A * | 2/2000 | Grudzien | 73/718 |
| 6,120,033 A | 9/2000 | Filippi et al. | 277/315 |
| 6,295,875 B1 * | 10/2001 | Frick et al. | 73/718 |
| 6,425,290 B2 | 7/2002 | Wilcox et al. | 73/715 |
| 6,484,585 B1 | 11/2002 | Sittler et al. | 73/718 |
| 6,508,129 B1 | 1/2003 | Sittler | 73/756 |
| 6,511,337 B1 | 1/2003 | Fandrey et al. | 439/320 |
| 6,523,454 B2 | 2/2003 | Rohner | 92/5 |

(Continued)

FOREIGN PATENT DOCUMENTS

BE        893-660        10/1982

OTHER PUBLICATIONS

"Notification of Transmittal of the International Search Report or the Declaration" PCT/US2005/045734, filed Dec. 15, 2005.

*Primary Examiner*—Phung T. Nguyen
(74) *Attorney, Agent, or Firm*—Westman, Champlin & Kelly, P.A.

(57) ABSTRACT

A diaphragm diagnostic system for use in an industrial field device has a diaphragm and a diagnostic feature. The diaphragm is configured to couple the field device to a process fluid and has a plurality of layers. A first layer of the plurality of layers is exposed to process fluid of an industrial process. A diagnostic feature is coupled to the diaphragm to monitor an electrical parameter of the diaphragm and responsively infer an operative state of the diaphragm based on a change in the monitored electrical parameter.

35 Claims, 6 Drawing Sheets

U.S. PATENT DOCUMENTS

| | | | |
|---|---|---|---|
| 6,577,140 B1 | 6/2003 | Wenman | 324/637 |
| 6,662,662 B1 | 12/2003 | Nord et al. | 73/715 |
| 6,684,711 B2 | 2/2004 | Wang | 73/724 |
| 6,782,754 B1 * | 8/2004 | Broden et al. | 73/753 |
| 6,941,853 B2 * | 9/2005 | Hembree | 92/98 R |
| 2002/0067255 A1 | 6/2002 | Tanizawa | 340/514 |
| 2004/0083883 A1 * | 5/2004 | Bubb et al. | 92/96 |

* cited by examiner

DIAGNOSTIC SYSTEM FOR DETECTING RUPTURE OR THINNING OF DIAPHRAGMS

BACKGROUND OF THE INVENTION

The present invention relates to diaphragms for use in industrial process instrumentation, and more particularly, to a diagnostic system for detecting rupture or thinning of diaphragms.

Many industrial instruments include a diaphragm element coupled to an industrial process for measuring a parameter of the process. For example, some pressure transmitters include an isolating diaphragm that is coupled to an industrial process. Pressure measurements may be taken directly from the diaphragm based on the diaphragms deflection in response to pressure or may be taken indirectly by a remote pressure sensor that is coupled to the isolating diaphragm by a fluid filled capillary. Rupture or thinning of the diaphragm can alter measurement readings, and/or permit process fluid to escape from the industrial process. Additionally, fill fluid from the fluid filled capillary may escape through a rupture in the isolating diaphragm to contaminate the process.

Conventionally, one technique for detecting rupture of the isolating diaphragm of a remote pressure sensor uses leads extending into the fluid fill. A measurement device coupled to the leads is adapted to detect a change in resistance between the two wires. If conductive process fluid flows through a rupture in the isolating diaphragm, the resistance between the leads changes, thereby indicating a rupture. Another technique is to monitor for an abrupt change in the transmitter measurement, which can indicate a rupture. However, these techniques only identify rupture of the diaphragm after the rupture has occurred, and potentially after fill fluid has leaked into the process.

There is an on-going need in the art for real-time detection of thinned or ruptured diaphragms. Embodiments of the present invention provide solutions to these problems and provide advantages over conventional diagnostic systems.

SUMMARY

A diaphragm diagnostic system for use in an industrial field device has a diaphragm and a diagnostic feature. The diaphragm couples the field device to a process fluid and has a plurality of layers. A first layer of the plurality of layers is exposed to process fluid of an industrial process. A diagnostic feature is coupled to the diaphragm to monitor an electrical parameter of the diaphragm and responsively infer an operative state of the diaphragm based on a change in the monitored electrical parameter.

DETAILED DESCRIPTION

Figure 1:
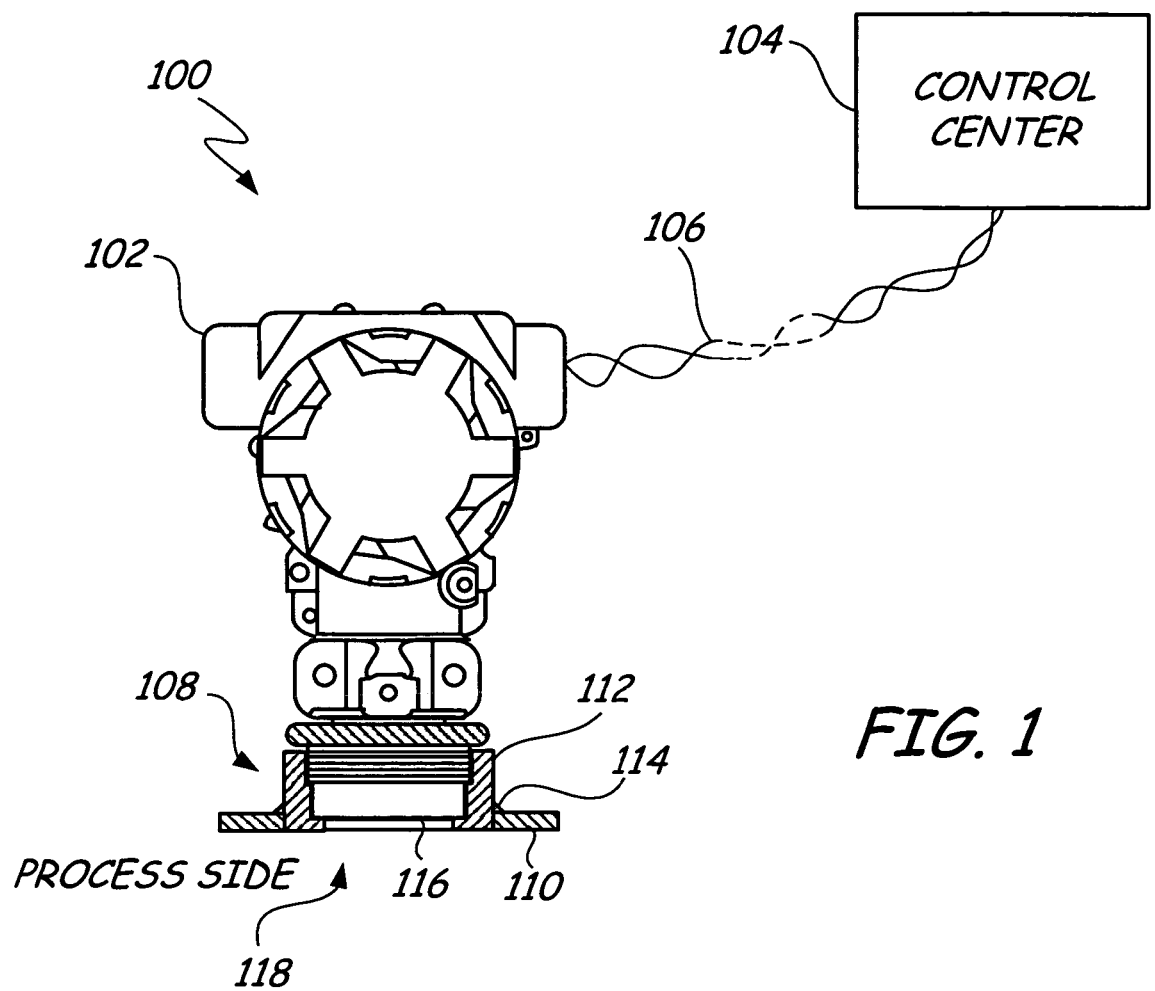
FIG. 1 is a simplified diagram of a process transmitter with an isolating diaphragm according to an embodiment of the present invention.

FIG. 1 is a simplified diagram of an industrial process transmitter with a rupture detection feature according to an embodiment of the present invention. The system 100 includes a transmitter 102 communicatively coupled to a control center 104 by a communications link 106, which may be wired or wireless. The communications link 106 couples electronics disposed within the housing of the transmitter 102 to monitoring and control systems in the control center 104.

Additionally, a base portion 108 of the transmitter 102 is coupled to a wall 110 of an industrial process vessel by a weld spud 112, which is welded to the vessel wall 110 at a weld joint 114. The transmitter 102 is threadably coupled to the weld spud 112 such that the isolating diaphragm 116 is directly exposed to process fluid within the vessel via an opening 118 in the vessel wall 110.

Figure 2:
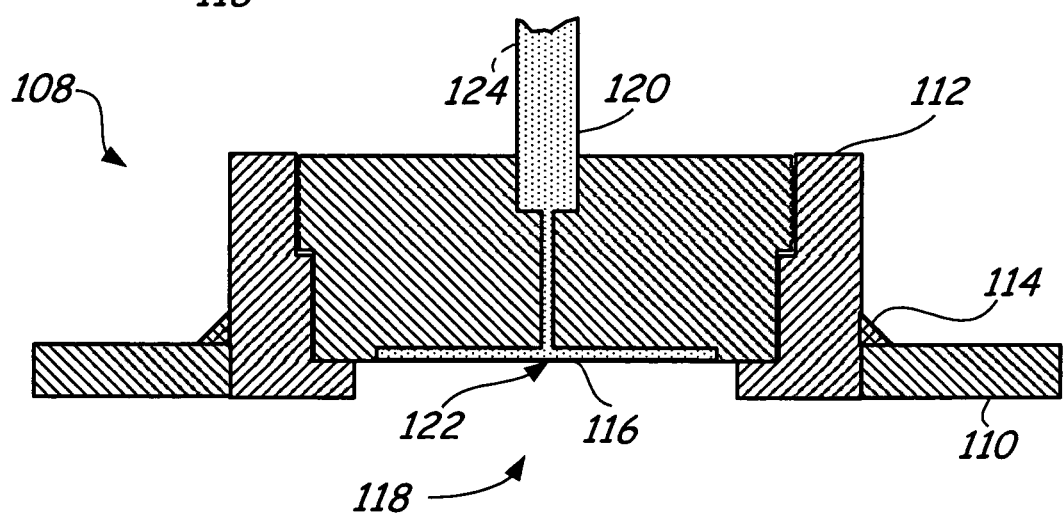
FIG. 2 is an enlarged, simplified cross-sectional view of the isolating diaphragm of FIG. 1.

FIG. 2 is an expanded cross sectional view of the base portion 108 of the transmitter 102 of FIG. 1. The base portion 108 is mounted to the vessel wall 110 by weld spud 112, which is attached t vessel wall 110 at weld joint 114. The isolating diaphragm 116 is directly exposed to process fluid through the opening 118 in the vessel wall 110 on one side and to a fluid-fill material 120 within a fluid-filled cavity 122 on the other side. Typically, changes in pressure of the process fluid against the isolating diaphragm 116 are translated through the fluid-fill 120 within the cavity 122 to a remote pressure sensor (not shown), which is coupled to the isolating diaphragm 116 via a fluid filled capillary 124.

Figure 3:
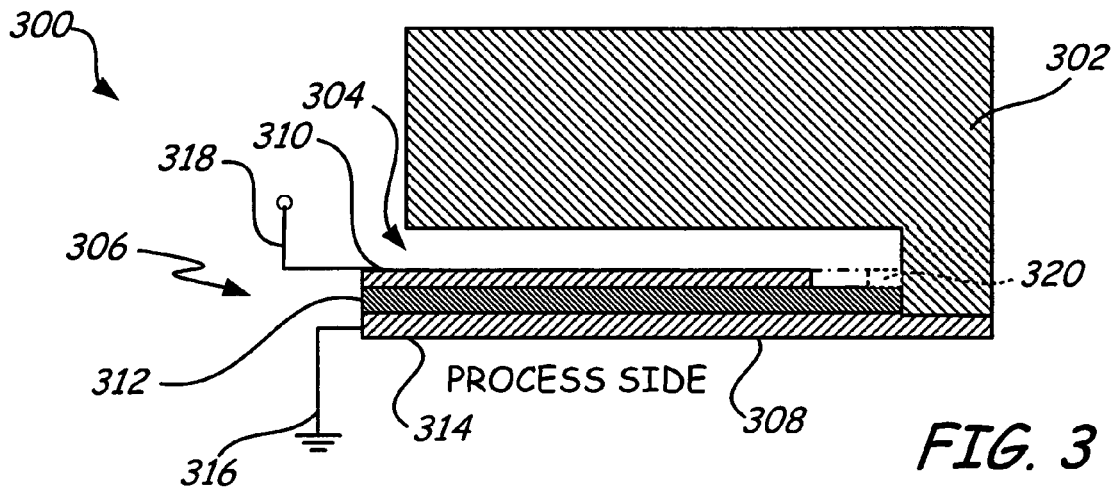
FIG. 3 is an enlarged cross-sectional view of the isolating diaphragm of FIG. 2 adapted for electronic detection of diaphragm thinning or rupture according to an embodiment of the present invention.

The isolating diaphragm 116 is a multi-layered capacitive structure (shown in detail in FIG. 3). Generally, the multi-layered isolating diaphragm 116 is sufficiently thin and flexible to deflect in response to process fluid pressure. The multi-layered diaphragm 116 is coupled to electronics disposed within the transmitter housing and adapted to provide electronic rupture indication according to an embodiment of the present invention.

FIG. 3 is an enlarged view of a portion the isolating diaphragm structure 300 according to an embodiment of the present invention. It should be understood that the isolating diaphragm structure 300 in FIG. 3 is not drawn to scale, but rather is exaggerated for explanatory purposes.

The isolating diaphragm structure 300 includes a transmitter 302 with a fluid-filled cavity 304 and an isolating diaphragm structure 306. The isolating diaphragm structure 306 is a multi-layered structure comprised of a first conductive layer 308 and a second conductive layer 310 separated by a dielectric material 312, which is preferably a solid dielectric material.

Preferably, the first conductive layer 308 has a surface 314 that is directly exposed to process fluid (a wetted surface). Typically, the first conductive layer 308 is electrically coupled to the process conduit, pipe or vessel, which is in turn coupled to an electrical ground 316. The second conductive layer 310 is provided with one or more leads 318 for measuring a change in capacitance or in complex impedance of the diaphragm structure 306.

Generally, capacitance is a ratio of charge to voltage potential. In a parallel plate capacitor, which is one type of capacitor contemplated by the present invention, the capacitance is determined according to the following formula:

$$C = \frac{\varepsilon_0 A}{d}$$

where $\varepsilon_0$ is a permittivity constant (dielectric constant), A represents the plate area, and d represents the distance separating the two plates. If, as in a preferred embodiment of the present invention, the dielectric is formed of a solid material, the distance (d) and the dielectric constant ($\varepsilon_0$) remain substantially constant. However, if the Area (A) of the plates changes (such as by corrosion or wear), the capacitance changes. Consequently, if a non-conductive material flowing through a pipe corrodes the first conductive plate 308, the Area (A) of the first conductive plate 308 changes, thereby causing a measurable change in the capacitance of the isolating diaphragm 306. A change in capacitance of the isolating diaphragm 306 can provide an indication that the isolating diaphragm 306 requires service or replacement.

If the process fluid within the pipe is non-conductive or is in a non-condensed gaseous form (or if the process pipe is empty, such as when the system is shut down), detection of rupture or thinning of the first conductive layer 308 can be inferred (as suggested above) by monitoring a capacitance on the second conductive layer 310 relative to the first conductive layer 308 (or relative to electrical ground). In general, the system 300 of the present invention is provided with a diagnostic feature (shown in FIG. 5) that is adapted to place a voltage or a signal on one or more layers of the capacitive diaphragm 306 and to measure a change. For example, in one embodiment, a voltage is applied across the capacitive diaphragm 306 and a time constant is evaluated to determine the capacitance. If the voltage is periodic, such as with a step voltage signal, a change in capacitance is detectable as a change in the time constant of the output signal. In this embodiment, the system 300 is adapted to detect thinning of the first conductive layer 308 by wear or corrosion based on a measured capacitance of the diaphragm 306.

In many cases, however, the process fluid is conductive, and corrosion of the first conductive layer 308 may not be detectable by measuring capacitance directly. Specifically, the process fluid of the industrial process may fill any holes or ruptures in the first conductive layer 308, thereby maintaining an apparently consistent surface area, such that the capacitance of the isolating diaphragm 306 does not change appreciably. Nevertheless, the corrosion may be inferred from a measured change in a complex impedance across the second conductive layer 310. For example, an equation for evaluating the state of the capacitance might resemble the following equation:

$$Z = \frac{V_m}{I_m} e^{-j\theta}$$

where Z represents a ratio of the magnitude of the voltage to the current multiplied by the exponential, which includes both real and imaginary parts. Given a change in the area of the first conductive plate 308, the impedance across the parallel plate capacitor (isolating diaphragm structure 306) may vary over time, even if the process fluid is conductive. A sensing circuit (such as signal analysis systems 514 in FIG. 5) can be coupled to the first conductive plate 308 and the second conductive plate 310 to measure an electrical parameter of the capacitive diaphragm 306, such as a complex impedance, a reactance, or other electrical parameter. By sweeping the second conductive plate with a time-varying signal (or with a signal containing a range of frequencies), a change in one or more of the electrical parameters may be used to infer the state of the first conductive layer.

In one embodiment, the dielectric material 312 comprises a porous material, such that if the process fluid corrodes through the first conductive layer 308, the process fluid passes through the dielectric material 312 to short the second conductive layer 310 to earth ground. With a porous dielectric, the failure of the first conductive layer 308 can be detected by an abrupt change in one or more electrical parameters of the diaphragm 306. In another embodiment, the dielectric material 312 can be selected to corrode to allow the influx of process fluid to contact the second conductive layer 310 and short the second conductive layer 310 to earth ground. If the dielectric material 312 is selected to be porous or corrodible, the second conductive layer 310 may be constructed to extend substantially a full extent of the dielectric layer 312 (as shown in phantom). Additionally, a non-conductive seal 320 (shown in phantom) can be disposed between the second conductive layer 310 and the transmitter 302 both to prevent leakage of process fluid past the second conductive layer 310 and to electrically isolate the second conductive layer 310 from the wall of transmitter 302.

In some instances, the process fluid can be volatile, and for intrinsic safety reasons, the capacitive diaphragm 306 can be adapted to prevent sparks or electrical discharge into leaking process fluid. For example, a voltage limiting device can be coupled to the capacitor to limit the voltage potential of the capacitor so as to prevent ignition of the volatile process fluid by sparks or discharge of electrical potential.

Figure 4:
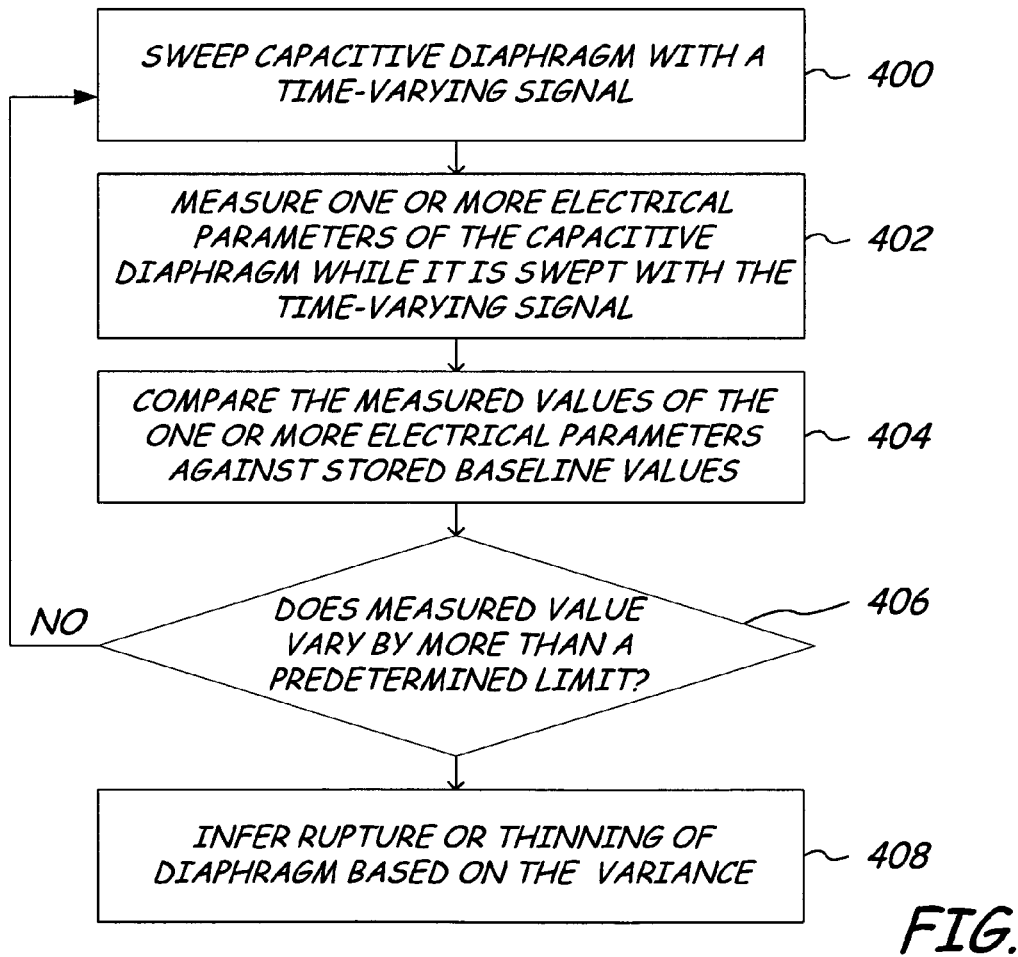
FIG. 4 is a simplified flow diagram of a process for inferring an operative state of an isolating diaphragm according to an embodiment of the present invention.

FIG. 4 is a simplified flow diagram of a process for inferring thinning or rupture of the diaphragm from a measured electrical parameter. The capacitive diaphragm is swept with a time-varying signal (block 400). One or more electrical parameters of the capacitive diaphragm are measured as the time-varying signal is applied (block 402). The measured electrical parameters are compared against stored baseline values (block 404). If the measured value varies from the baseline value by more than a predetermined limit (block 406), rupture or thinning of the diaphragm may be inferred based on the variance (block 408). If the measured value does not vary from the baseline by more than the predetermined limit (block 406), steps 400 and sequence are repeated.

In general, the measured electrical parameter can be a capacitance or can be any number of complex electrical parameters (such as an impedance, a reactance, an admittance, and the like). If thinning or rupture is inferred based on a variance from the stored baseline, an alarm signal indicative of the inferred operative state of the capacitive diaphragm can be generated and sent to a control center. It should be understood that the operative state may range from an inoperative or non-operative state to a fully operative state. Moreover, it should be understood that a magnitude or extent of the variance can be indicative of the extent of corrosion, wear or damage to the capacitive diaphragm. Alternatively, the extent of the variance may be indicative of the type of corrosion, wear or damage (such as pitting, cracking, even-wear, corrosion, and so on), depending on which of the electrical parameters varies from the baseline measurement. A cracked or fully ruptured diaphragm may be detected as an open circuit or infinite impedance, whereas variations from a reference value can be indicative of a deteriorating state of the isolating diaphragm.

In one embodiment, the swept signal is triggered by a control center. In an alternative embodiment, the swept signal analysis is triggered by the diagnostic circuitry and is performed periodically. While the method of FIG. 4 utilizes a time-varying signal, in some instances, an applied DC voltage can also be utilized. Finally, expert systems, such as fuzzy logic systems, artificial intelligence systems, neural networks and the like, can be utilized to analyze electrical parameters of the isolating diaphragm to infer an operative state of the diaphragm.

Figure 5:
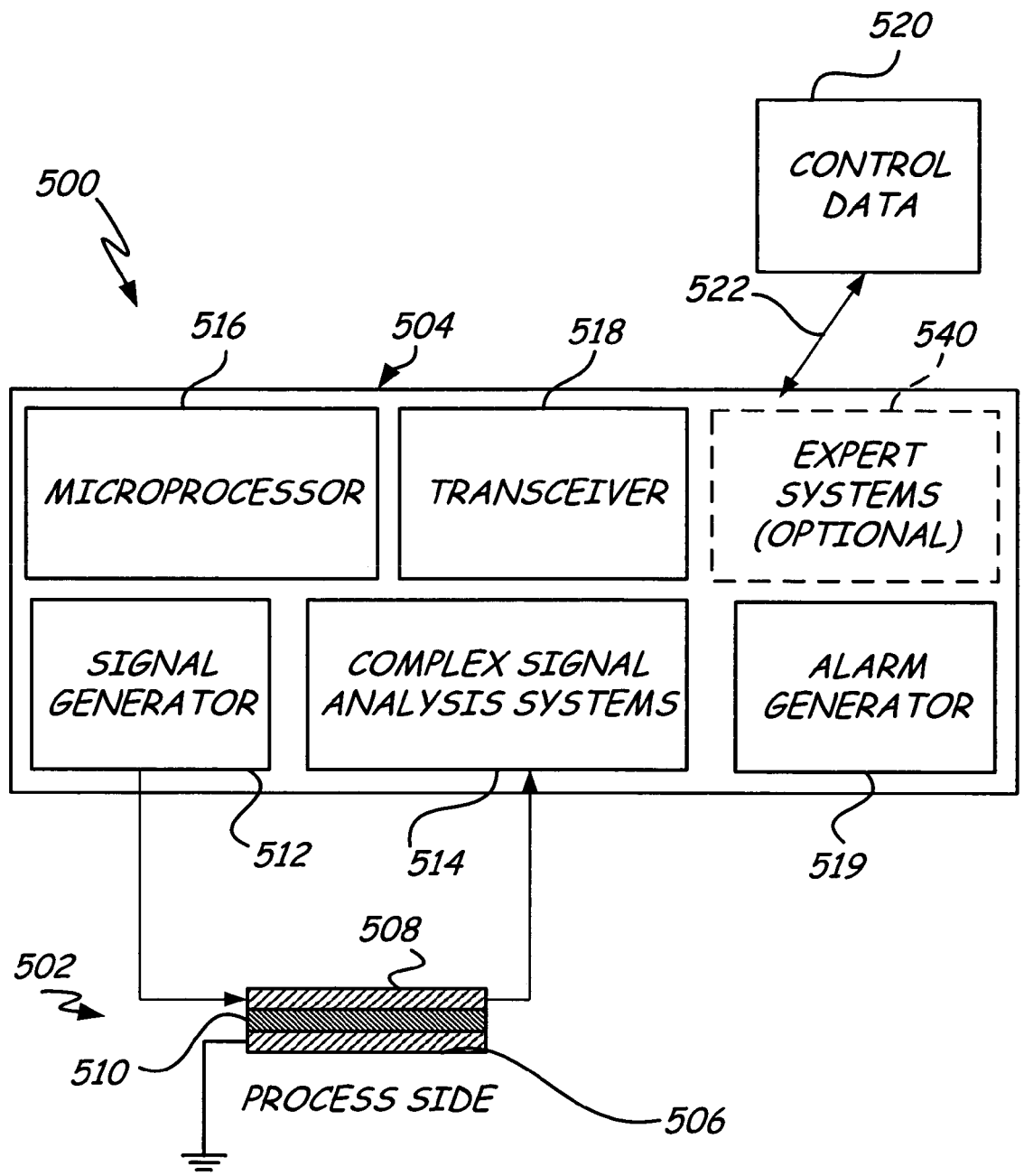
FIG. 5 is a simplified block diagram of an electronic diagnostic system according to an embodiment of the present invention.

FIG. 5 is a simplified block diagram of a diagnostic system 500 according to an embodiment of the present. The diagnostic system 500 includes an isolating diaphragm structure 502 communicatively coupled to a diagnostic feature 504 (which can be implemented in circuitry), which is typically enclosed in a housing. The diaphragm structure includes a first conductive layer 506 and a second conductive layer 508 separated by a dielectric material 510. The first conductive layer 506 is exposed to the process fluid within a conduit or pipe of an industrial process. In one embodiment, the first conductive layer 506 is electrically grounded to the conductive pipe wall. The second conductive layer 508 is isolated from the process fluid and electrically isolated from the first conductive layer 506.

The diagnostic feature 504 includes a signal generator 512, complex signal analysis systems 514, microprocessor 516, transceiver 518, an alarm generator 519, and optionally expert systems 540, such as artificial intelligence systems, fuzzy logic systems, neural networks, and the like. The signal generator 512 is circuitry adapted to transmit an electrical signal, such as a time-varying or periodic signal. The signal generator 512 transmits an electrical signal over the second conductive layer 508, which can be measured and analyzed by complex signal analysis systems 514 to detect a change in one or more complex electrical parameters of the system. The expert systems 540 can be used to analyze one or more electrical parameters and to infer an operative state of the isolating diaphragm based on changes to one or more of the electrical parameters relative to a stored baseline measurement. It should be understood that the signal analysis systems 514 may comprise a single processor, circuitry adapted to process measured signals, a capacitive sensor, or any other element adapted to derive a diagnostic measure based on the measured capacitance.

In one embodiment, the process fluid being monitored is non-conductive, and the analysis systems 514 comprise a sensor adapted to measure a capacitance of the isolating diaphragm 502 relative to electrical ground. In environments where the process fluid is electrically conductive, the signal generator 512 is preferably adapted to sweep the second conductive layer 508 with electrical signals having a range of frequencies. The complex signal analysis systems 514 are adapted to detect a complex impedance of the isolating diaphragm 502 within the range of swept frequencies.

The microprocessor 516 may be utilized to further process the measured complex impedance and/or to compare the measured complex impedance against stored values to detect alarm conditions. An alarm condition may be inferred from a detected change that varies from a baseline measurement by more than a predetermined amount. The microprocessor 516 is preferably adapted to compare the measured change in impedance against a predetermined limit, and to generate an alarm for transmission by transceiver 518 to a control center 520 via communications link 522 if the measured change exceeds the limit. Alternatively, a separate alarm generator 519 (or alarm generation circuitry) may be utilized to generate the alarm signal for transmission by the transceiver 518. In one embodiment, if the process fluid is non-conductive, the complex signal analysis systems 514 can simply measure a capacitance of the isolating capacitor 502, and a change in capacitance that exceeds a predetermined limit can cause the processor 516 to generate an alarm.

It should be understood that elements of the diagnostic system 500 may be shared with other components of the transmitter electronics 504. For example, the transceiver 518 may also be used by a sensing element or complex signal analysis systems 514, directly, for example, to transmit raw data to a control center. Similarly, the control center 520 may send a control signal via transceiver 518, causing the sensing element (such as analysis systems 514) to take a new measurement. Various components such as the signal generator 512, complex signal analysis system 514, and alarm generator 519 can be implemented wholly or partially in microprocessor 516.

Figure 6:
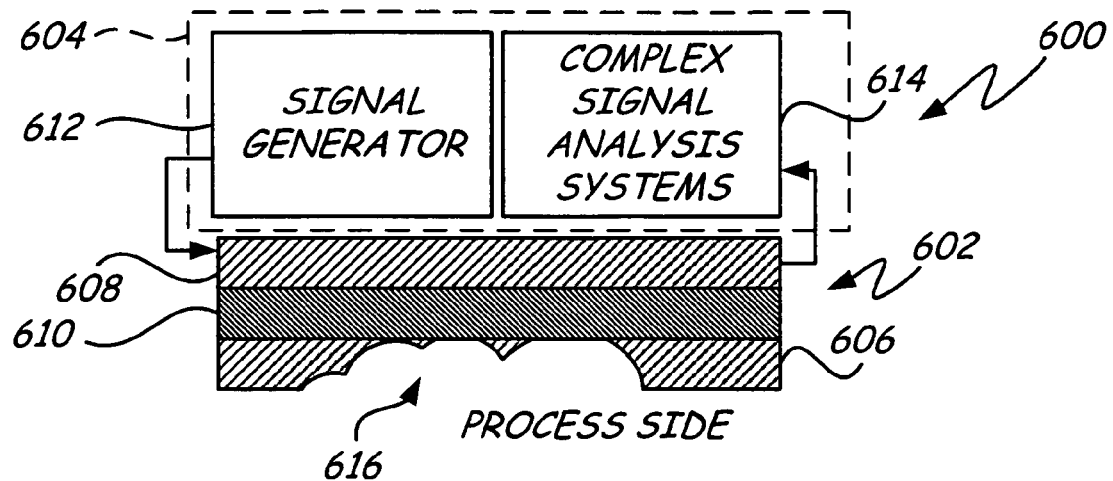
FIG. 6 is a simplified block diagram of the electronic diagnostic system after corrosion or thinning by the process fluid has occurred according to an embodiment of the present invention.

FIG. 6 is a simplified block diagram of a diagnostic system 600 according to an embodiment of the present invention. The system 600 includes an isolating capacitive diaphragm 602 coupled to a diagnostic electronics 604. The diaphragm 602 includes a first conductive layer 606 and a second conductive layer 608 separated by a dielectric 610. A signal generator 612 and complex signal analysis systems 614 are electrically coupled to the second conductive layer 608.

In this embodiment, the process fluids within a tank have corroded the first conductive layer 606, leaving pits or openings 616 in the first conductive layer 606, partially exposing the dielectric 610 to the process fluid. The dielectric 610 is preferably formed from a solid material so that breach of the first conductive layer 606 does not release dielectric fluid into the process fluid. Additionally, a solid dielectric 610 serves as a layer of protection against leaking of the capillary fill fluid into the process fluid (in a remote seal system, for example). Moreover, a solid dielectric 610 serves as a layer of protection against leaking of the process fluid into the electronics housing (for example, if the electronics are directly adjacent to the process).

The signal generator 612 is coupled to the second conductive layer 608 and adapted to transmit signals in a particular range of frequencies onto the second conductive layer 608. The complex signal analysis system 614 is coupled to the second conductive layer 608 and adapted to detect changes in the swept signal based on a change in the first conductive layer 606.

In one embodiment, if the process fluid is non-conductive, the corrosion of the first conductive layer 606 may be detected as a change in the capacitance (or electrical potential) between the first and second conductive layers 606,608. However, if, as is more common, the process fluid is conductive, the signal generator 612 can sweep the second conductive layer 608 with a range of test frequencies (or any time-varying signal), and the complex signal analysis systems 614 can be utilized to detect the corrosion based on changes in the complex impedance. In either case, if the measured change exceeds a predetermined limit, an alarm may be generated and transmitted to a control center.

Figure 7:
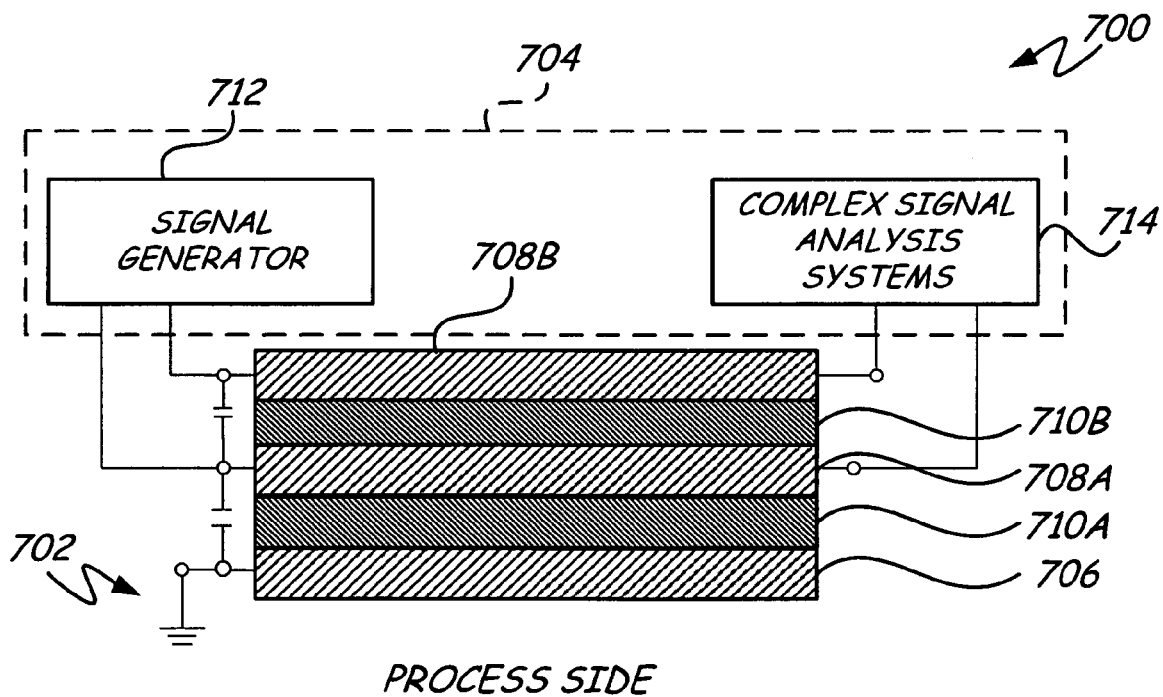
FIG. 7 is a simplified block diagram of an alternative embodiment of the electronic diagnostic system according to an embodiment of the present invention.

FIG. 7 illustrates a simplified block diagram of a diagnostic system 700 according to an embodiment of the present invention. The diagnostic system 700 includes a multi-layered isolating diaphragm structure 702 coupled to a transmitter 704. The isolating diaphragm structure 702 is formed from three layers of conductive material 706, 708A and 708B separated from one another by dielectric material layers 710A and 710B. A signal generator 712 is coupled to the second and third conductive layers 708A and 708B, respectively, while the first conductive layer 706 is coupled to the process conduit, and therefore grounded. A complex signal analysis system 714 is coupled to the second and third conductive layers 708A and 708B, respectively, to monitor changes in complex impedance or capacitance between each of the first and second conductive layers 706 and 708A, respectively, and the second and third conductive layers 708A and 708B, respectively. A differential change in capacitance or complex impedance may be indicative of a rupture of the first conductive layer 706.

In one embodiment, the process fluid is non-conductive or in a gaseous state, and corrosion of the first conductive layer 706 is detected based on a change in the capacitance of the diaphragm 702 measured directly. Alternatively, if the process fluid is conductive, corrosion of the first conductive layer 706 is inferred from a change in a complex impedance of the diaphragm structure 702. Specifically, the signal generator 712 is adapted to sweep a signal with a range of frequencies over the isolated conductive layers 708A and 708B, and the complex signal analysis systems 714 are adapted to detect a change in a complex impedance of the diaphragm 702. Thinning, wear or corrosion of the first conductive layer 706 may be inferred from a change in the complex impedance.

In general, the present invention provides a number of advantages over the prior art. First, by replacing the thin foil isolating diaphragm with a multi-layer diaphragm adapted to provide a capacitive indication (or electronic indication) of thinning or rupture, the transmitter can be adapted to diagnose itself and to provide an alarm indicative of the need for servicing of the isolating diaphragm before the diaphragm ruptures and contaminates the process. Second, the dialectric material can be a solid non-conductive material, such as ceramic, which maintains isolation between a process fill fluid (such as that used within an isolating diaphragm) and the process fluid of the industrial process, even after the whetted surface of the isolating element ruptures. Third, different implementations of the isolating element diagnostic may provide additional details about the status of the isolating element. In particular, a two plate diagnostic system may provide a raw indication of rupture or thinning, whereas a three or more plate diagnostic system may provide a more complex and instructive indication of the extent of damage to the isolating element, based, in part, on a differential capacitance. Additionally, the present invention is applicable to any industrial instrument, which has a thin area that is susceptible to corrosion or damage from the process fluid. Thus, the present invention provides an isolating element adapted to generate an electrical signal indicative of potential damage to the isolating element before such damage becomes too extensive.

Figure 8:
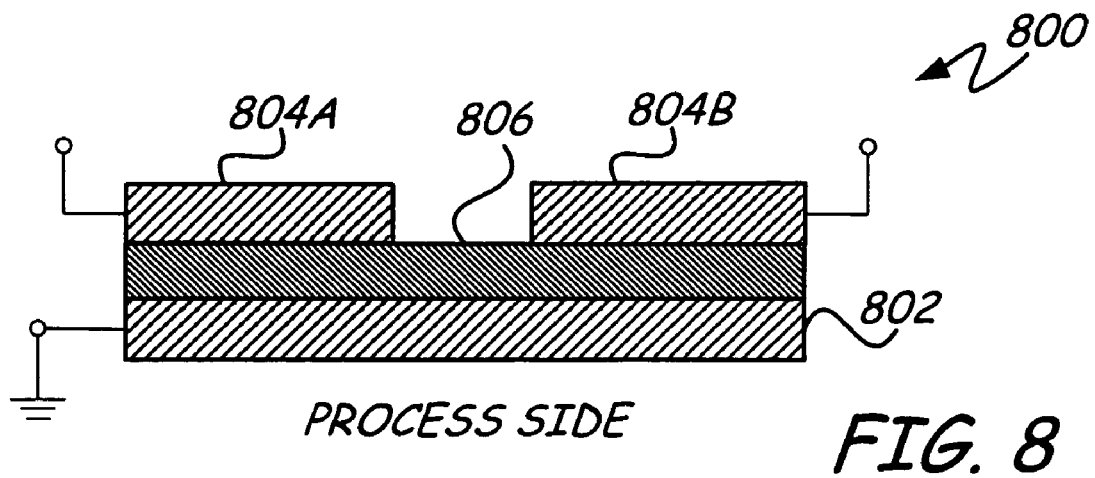
FIG. 8 is a simplified block diagram of an alternative embodiment of the electronic diagnostic system according to an embodiment of the present invention.

FIG. 8 is a simplified block diagram of an alternative isolating diaphragm structure 800 according to an embodiment of the present invention. The isolating diaphragm structure 800 is comprised of a first conductive layer 802 and a second conductive layer 804 divided into two electrically separate plates 804A and 804B and separated from the first conductive layer 802 by dielectric 806. In this embodiment, a change in the area of the first conductive layer 802, such as by corrosion, may be detected as a differential capacitance measured from plates 804A and 804B. In an alternative embodiment, a complex impedance measurement may be utilized, as discussed above. In this instance, the complex impedance is measured across both plates 804A and 804B separately, based on generated signals. In one embodiment, a phase difference measured from the two plates 804A and 804B based on the same signal may be indicative of corrosion.

In this embodiment, a capacitance is measurable from or between these two half-plates 804A and 804B. The measured capacitance may be altered by a change in area caused by corrosion of the first conductive layer 802. However, if the process fluid is conductive, direct measurement of capacitance may not reveal anything about the condition of the first conductive layer 802. In this instance, if the process fluid is conductive, the first plate half-plate 804A may be swept with a range of frequencies. The second half-plate 804B may be monitored for a change in phase or amplitude of a measured signal at a particular range of frequencies. A change in the measured output may be indicative of a change in area of the first conductive layer 802. Process related corrosion, thinning or wear may be inferred depending on the specific change in the measured output.

Figure 9A:
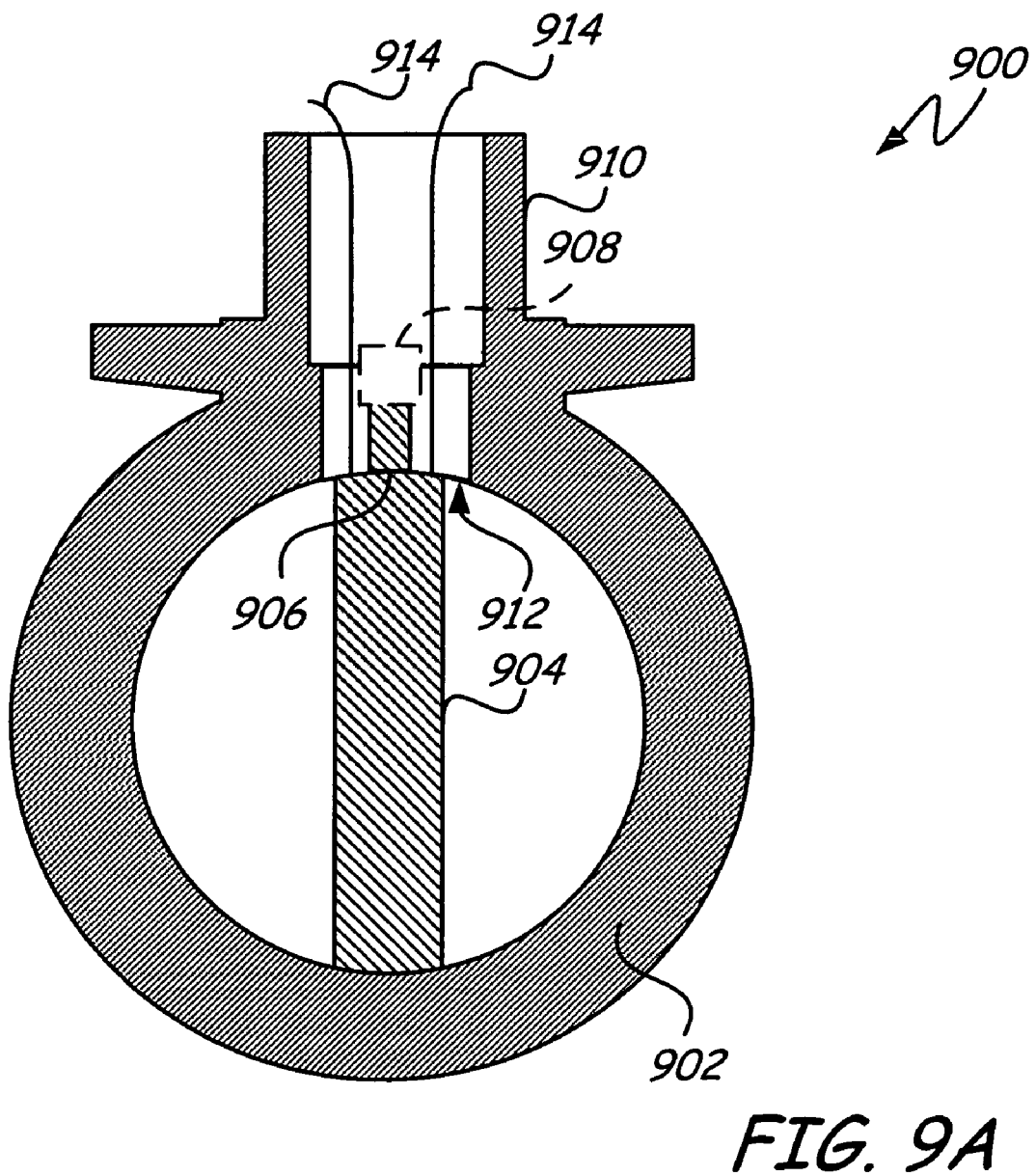
FIG. 9A is a simplified cross-sectional view of an electronic rupture diagnostic system adapted to detect thinning or rupture of the thinned-wall portion of a vortex flowmeter according to an embodiment of the present invention.

FIG. 9A is a simplified cross-sectional view of a vortex flowmeter system incorporating the capacitive isolating diaphragm of the present invention in a thin-wall portion of the pipe wall. A pipe 902 is divided into two flow paths by a shedding bar 904. The shedding bar 904 extends from a thin wall portion 912 of the pipe wall and is coupled to post 906 such that shedding or oscillatory motion of the shedding bar 904 caused by fluid vortices within the pipe 902 are detectable from movement or vibration of the post 906. A sensor 908 (shown in phantom) is typically coupled to the post 906 to measure fluid velocity within pipe 902 based on movement of the post 906. Generally, the sensor 908 and other process electronics are disposed outside of the pipe 902 and in a transmitter housing 910.

In general, the shedding bar 904 is coupled post 906 via the thin wall portion 912. The thin wall portion 912 is preferably sufficiently thin to transmit shedding bar motion through the pipe wall to the post 906, where the sensor 908 is adapted to measure fluid flow rate of fluid within the pipe 902 based on the motion of the post 906. One problem that arises, particularly in high pressure environments, involves maintaining sufficient thickness in the thin wall portion 912 to prevent rupture of the wall at high pressure while still allowing sufficient flexibility for movement. Leads 914 may be provided for connection to diagnostic circuitry.

The multi-layered isolating diaphragm of the present invention may be used in such applications to provide isolation from the process fluid as well as rupture diagnostics.

Figure 9B:
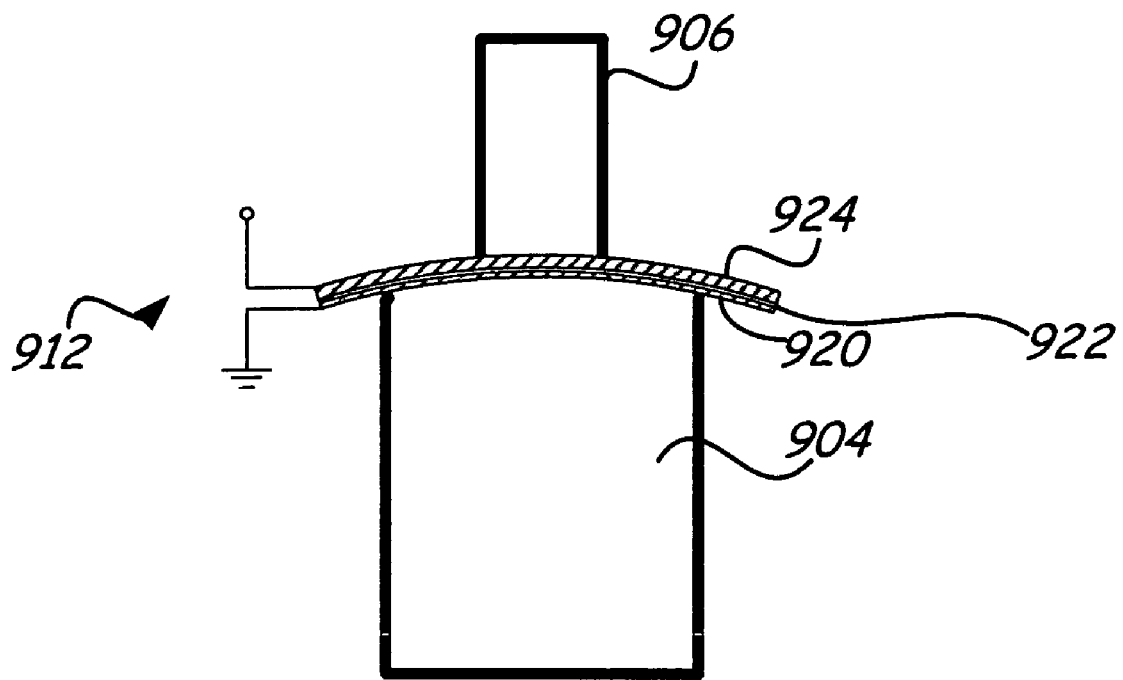
FIG. 9B is an expanded cross-sectional view of the thinned wall portion of the vortex flowmeter of FIG. 9A.

FIG. 9B is an expanded cross-sectional view of the flow meter element 900 with a thin wall portion 912 formed from any one of the isolating capacitive diaphragm structures described above with respect to FIGS. 3 and 5-7. In this embodiment, the diaphragm structure 912 is a capacitive structure 926. The capacitive structure 926 is formed from a first conductive layer 920 coupled to the wall of the pipe and exposed to the process fluid directly adjacent to the shedding bar 904. A second conductive layer 924 is separated from the first conductive layer 920 by dielectric material 922. The second conductive layer 924 is isolated from the process fluid outside of the pipe and adjacent to the post 906. Leads 914 may be provided from the second conductive layer to detect a change in complex impedance and/or in capacitance of the capacitive structure 926.

In this embodiment, the dielectric 922 is preferably a solid non-conductive material. The layers of the capacitive structure 926 provide added durability, while providing a means for detecting corrosion or wear of the first conductive layer 920. In particular, by monitoring the complex impedance and/or capacitance of the capacitive structure 926, corrosion or wear of the thin wall portion 912 may be detected before a rupture or breach occurs, thereby preventing unplanned shut down and/or exposure of sensitive electronics in the transmitter housing to process fluid from the pipe.

In general, the present invention makes use of the observation that capacitance is proportional to the surface area of the plates in a parallel plate arrangement. If the layer of foil closest to the process begins to thin or rupture, then the effective area of the diaphragm is changed by the size of the rupture or by the extent of thinning. This change in the effective area of the diaphragm causes a change in the measured capacitance of the parallel plates.

This assumes that the process fluid being measured is non-conductive. In such an instance, if the capacitance of the diaphragm is continuously monitored, then corrosion, wear, erosion or pitting will result in a measurable change in capacitance. This measurable change provides an early indication of potential problems with the isolating diaphragm or thin wall portion. Circuitry coupled to the capacitive isolating element could then immediately alert a control center that a rupture has occurred or that the isolating diaphragm or thin wall portion may need service.

In many industrial processes, the process fluid in contact the isolating diaphragm is itself conductive. In such an instance, direct measure of capacitance between the layers of foil may not reflect a measurable change in capacitance as the process-exposed foil becomes corroded. Specifically, the conductive process fluid may flow into the corroded areas of the foil, thereby completing or replacing the eroded foil areas with conductive fluid. In such an instance, the measured capacitance may remain unchanged. However, a circuit adapted to measure complex electrical parameters, such as a complex impedance, a reactance, and the like, can be used to measure a swept frequency. Changes in one or more of the complex electrical parameters may reflect a hole, thinning or other changes to the process-exposed foil of the isolating diaphragm under various operating conditions. A single generation circuit can be utilized to sweep one of the foil layers and a sensing circuit can be utilized to measure the swept frequency, which may change in the event that one or more of the foil layers is damaged by process fluid.

Generally, the systems and methods of the present invention monitor electrical parameters of a capacitive isolating diaphragm. One or more of the electrical parameters can change if the isolating diaphragm thins, corrodes, or is otherwise damaged during operation. Signal analysis systems can compare measured parameters against stored baseline parameters. Alternatively, the signal analysis systems include expert systems adapted to infer an operative state of the diaphragm based on a change in electrical parameters over time. The electrical parameters can include capacitance. Alternatively, the electrical parameters can include complex electrical parameters, such as complex impedance, reactance, admittance, and the like. Finally, the process fluid can be in a liquid state or a gaseous state.

Although the present invention has been described with reference to preferred embodiments, workers skilled in the art will recognize that changes may be made in form and detail without departing from the spirit and scope of the invention.

What is claimed is:

1. A diaphragm diagnostic system for use in an industrial field device comprising:
    a diaphragm configured to couple the field device to a process fluid, the diaphragm comprising a plurality of layers, a first layer of the plurality of layers exposed to the process fluid of an industrial process; and
    a diagnostic circuit coupled to the diaphragm to monitor an electrical parameter of the diaphragm and responsively infer an operative state of the diaphragm based on a change in the monitored electrical parameter, wherein the electrical parameter is a function of an applied time varying signal.

2. The diaphragm diagnostic system of claim 1 and further comprising:
    an alarm generation feature adapted to generate an alarm signal indicative of the inferred operative state of the diaphragm if the change exceeds a predetermined limit.

3. The diaphragm diagnostic system of claim 1 wherein the electrical parameter comprises a capacitance of the diaphragm.

4. The diaphragm diagnostic system of claim 1 further comprising:
    a signal generator adapted to sweep the isolating diaphragm with the time-varying signal, wherein the electrical parameter comprises a complex electrical parameter of the diaphragm.

5. The diaphragm diagnostic system of claim 4 further comprising:
    complex signal analysis systems adapted to monitor the diaphragm to detect changes in the electrical parameter relative to a stored baseline signal based on the time-varying signal.

6. The diaphragm diagnostic of claim 1 wherein the plurality of layers comprises:
    at least one electrically conductive layer.

7. The diaphragm diagnostic of claim 1 wherein the plurality of layers comprises:
    at least one dielectric layer.

8. The diaphragm diagnostic of claim 1 wherein the plurality of layers comprises:
    at least two electrically conductive layers; and
    at least one dielectric layer separating the at least two electrically conductive layers.

9. The diaphragm diagnostic of claim 8 wherein the electrical parameter comprises a capacitive potential of the at least two conductive layers.

10. The diaphragm diagnostic system of claim 1 wherein an extent of the change is indicative of an extent of change in a surface area of the first conductive layer.

11. The diaphragm diagnostic system of claim 1 wherein the diagnostic circuit is adapted to monitor one or more electrical parameters of the plurality of conductive layers relative to the first layer.

12. A method for inferring an operative state of an isolating diaphragm, the method comprising:
provAiding an isolating diaphragm comprised of a plurality of layers, a first layer of the plurality of layers exposed directly to a process fluid;
applying an electrical signal to the isolating diaphragm; and
inferring responsively an operative state of the isolating diaphragm from a measured change in an electrical parameter of the isolating diaphragm relative to the applied electrical signal; and
wherein the electrical signal has a time-varying component.

13. The method of claim 12 further comprising:
generating an alarm signal indicative of a non-operative state of the isolating diaphragm if the measured change exceeds a predetermined limit.

14. The method of claim 12 further comprising:
generating an alarm signal indicative of a deteriorating state of the isolating diaphragm if the measured change exceeds a predetermined limit.

15. The method of claim 12 wherein the step of applying comprises:
generating an electrical signal comprised of a range of frequencies; and
transmitting the range of frequencies over the isolating diaphragm.

16. The method of claim 12 wherein the step of inferring comprises:
monitoring an electrical parameter of the isolating diaphragm; and
calculating a change in the monitored electrical parameter relative to a stored baseline measurement.

17. The method of claim 12 wherein the electrical parameter comprises a time constant of the isolating diaphragm.

18. The method of claim 12 wherein the electrical parameter comprises a complex electrical parameter of the isolating diaphragm.

19. The method of claim 12 wherein the plurality of layers comprises at least one electrically conductive layer.

20. The method of claim 12 wherein the plurality of layers comprises at least one dielectric layer.

21. The method of claim 12 wherein the plurality of layers comprises:
at least two electrically conductive layers; and
at least one dielectric layer separating the at least two electrically conductive layers.

22. A diaphragm diagnostic system for use in an industrial field device comprising:
a capacitive element configured to couple the field device to a process fluid, the capacitive element comprised of a plurality of layers, a first layer of the plurality of layers exposed to the process fluid of an industrial process; and
a diagnostic circuit coupled to the capacitive element to monitor an electrical parameter of the capacitive element and responsively infer an operative state of the capacitive element based on a change in the monitored electrical parameter.

23. The diaphragm diagnostic system of claim 22 wherein the industrial field device comprises a vortex flow meter having a shedding bar extending into a pipe section, and wherein the capacitive element comprises a thin wall portion of the pipe section through which motion of the shedding bar due to fluid flow within the pipe is translated.

24. The diaphragm diagnostic system of claim 22 wherein the industrial field device comprises a pressure sensor coupled to a pipe section, and wherein the capacitive element comprises a flexible isolating diaphragm adapted to translate pressure from fluid flow within the pipe section through a fluid filled capillary to a remote sensor.

25. The diaphragm diagnostic system of claim 22 further comprising:
an alarm generation feature adapted to generate an alarm signal indicative of the inferred operative state for transmission to a control center.

26. The diaphragm diagnostic system of claim 22 wherein a magnitude of the change is indicative of an extent of damage to the capacitive element.

27. The diaphragm diagnostic system of claim 22 wherein the measured change comprises a complex impedance of the capacitive element.

28. The diaphragm diagnostic system of claim 22 wherein the diagnostic circuit further comprises:
a signal generator adapted to sweep the capacitive element with an electrical signal having a time-varying component; and
complex signal analysis systems adapted to monitor the capacitive element and to infer the operative state of the capacitive element based on a change in one or more electrical parameters of the capacitive element relative to a stored baseline measurement.

29. The diaphragm diagnostic system of claim 22 wherein the diagnostic circuit is adapted to monitor one or more electrical parameters of the plurality of conductive layers relative to the first layer.

30. The diaphragm diagnostic system of claim 22 wherein the plurality of layers comprises:
at least one electrically conductive layer.

31. The diaphragm diagnostic system of claim 22 wherein the plurality of layers comprises:
at least one dielectric layer.

32. The diaphragm diagnostic system of claim 22 wherein the plurality of layers comprises:
at least two electrically conductive layers; and
at least one dielectric layer separating the at least two electrically conductive layers.

33. The diaphragm diagnostic system of claim 32 wherein the at least one dielectric layer comprises a porous material.

34. The diaphragm diagnostic system of claim 33 wherein the operative state is inferred based on an abrupt change in the electrical parameter if the process fluid leaks through the first layer.

35. The diaphragm diagnostic system of claim 22 wherein the electrical parameter is a function of an applied time varying signal.

* * * * *